US010182706B2

(12) United States Patent
Sato (10) Patent No.: US 10,182,706 B2
(45) Date of Patent: Jan. 22, 2019

(54) INSERTION DEVICE TREATMENT SYSTEM

(71) Applicant: OLYMPUS CORPORATION, Tokyo (JP)

(72) Inventor: Yosuke Sato, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/465,922

(22) Filed: Mar. 22, 2017

(65) Prior Publication Data

US 2017/0188797 A1    Jul. 6, 2017

Related U.S. Application Data

(63) Continuation of application No. PCT/JP2016/059687, filed on Mar. 25, 2016.

(30) Foreign Application Priority Data

May 20, 2015 (JP) ................. 2015-102331

(51) Int. Cl.
*A61B 1/00* (2006.01)
*A61B 5/06* (2006.01)
(Continued)

(52) U.S. Cl.
CPC ...... *A61B 1/00156* (2013.01); *A61B 1/00006* (2013.01); *A61B 1/0016* (2013.01);
(Continued)

(58) Field of Classification Search
CPC .............. A61B 1/00156; A61B 1/0016; A61B 1/00071; A61B 1/008; A61B 1/00105;
(Continued)

(56) References Cited

U.S. PATENT DOCUMENTS 7,212,737 B2 * 5/2007 Dehmel ................. A61B 1/042
348/68
2005/0191046 A1    9/2005 Dehmel et al.
(Continued)

FOREIGN PATENT DOCUMENTS

CN    104203076 A    12/2014
JP    2007-185380 A    7/2007
(Continued)

OTHER PUBLICATIONS

Graco Owner's Manual, 2012, 26 pages.*
(Continued)

*Primary Examiner* — Timothy J Neal
(74) *Attorney, Agent, or Firm* — Scully, Scott, Murphy & Presser, P.C.

(57) ABSTRACT

An insertion device includes an insertion section extended along a longitudinal axis, and an assist tool detachably attached to the insertion section. The assist tool is actuated with being attached to the insertion section, thereby causing a propulsion force for movement along the longitudinal axis to act on the insertion section. A moving member movable between a first position and a second position is provided in one of the insertion section and the assist tool. The moving member is held at the second position due to a pressure from the other of the insertion section and the assist tool, in a state that the assist tool is located at the specific position relative to the insertion section.

6 Claims, 9 Drawing Sheets

(51) Int. Cl.
*A61B 1/05* (2006.01)
*A61B 1/06* (2006.01)
*A61B 1/07* (2006.01)

(52) U.S. Cl.
CPC ............ *A61B 1/00133* (2013.01); *A61B 1/05* (2013.01); *A61B 1/0676* (2013.01); *A61B 1/07* (2013.01); *A61B 5/062* (2013.01)

(58) Field of Classification Search
CPC ............ A61B 1/00133; A61B 1/00135; A61B 1/0014; A61B 5/062
See application file for complete search history.

(56) References Cited

U.S. PATENT DOCUMENTS

| | | | |
|---|---|---|---|
| 2008/0262309 A1 | 10/2008 | Miyoshi et al. | |
| 2013/0035552 A1 | 2/2013 | Moriyama | |
| 2014/0296771 A1* | 10/2014 | Naito | F16C 1/06 604/19 |
| 2014/0323805 A1* | 10/2014 | Naito | A61B 1/00071 600/114 |

FOREIGN PATENT DOCUMENTS

| | | | |
|---|---|---|---|
| JP | 2008-43361 A | 2/2008 | |
| JP | 5326049 B2 | 10/2013 | |
| WO | 2008/018256 A1 | 2/2008 | |
| WO | WO-201434532 | * 3/2014 | ............... A61B 1/00 |

OTHER PUBLICATIONS

Chinese Office Action dated Nov. 27, 2017 in Chinese Patent Application No. 201680003135.0.
International Preliminary Report on Patentability with the Written Opinion dated Nov. 30, 2017 received in International Application No. PCT/JP2016/059687.
International Search Report dated Jun. 21, 2016 received in PCT/JP2016/059687.
Chinese Office Action dated May 9, 2018 received in CN 201680003135.0.

* cited by examiner

INSERTION DEVICE TREATMENT SYSTEM

CROSS-REFERENCE TO RELATED APPLICATIONS

This is a Continuation Application of PCT Application No. PCT/JP2016/059687, filed Mar. 25, 2016 and based upon and claiming the benefit of priority from prior Japanese Patent Application No. 2015-102331, filed May 20, 2015, the entire contents of which are incorporated herein by reference.

BACKGROUND OF THE INVENTION

1. Field of the Invention

The present invention relates to an insertion device including an insertion section extended along a longitudinal axis, and an assist tool detachably attached to the insertion section and actuated to cause a propulsion force for movement along the longitudinal axis to act on the insertion section.

2. Description of the Related Art

Japanese Patent No. 5326049 discloses an endoscope device (insertion device) including an insertion section extended along a longitudinal axis, and an assist tool (spiral unit) attached to the insertion section to be rotatable around the longitudinal axis. In the endoscope device, a motor (driving source) attached to a held section (operation section) of an endoscope is driven, thereby transmitting a driving force generated by the motor to the assist tool attached to the insertion section via a shaft or the like extended inside the insertion section. The transmission of the driving force causes the assist tool to rotate relative to the insertion section around the longitudinal axis. A fin spirally extended around the longitudinal axis is provided on an outer peripheral surface of the assist tool. As the assist tool rotates around the longitudinal axis with the fin pressed by a lumen wall or the like, a propulsion force acts on the insertion section and the assist tool toward one side in a direction along the longitudinal axis. In other words, the propulsion force to move the insertion section along the longitudinal axis acts on the insertion section.

BRIEF SUMMARY OF THE INVENTION

According to one aspect of the invention, an insertion device including: an insertion section which is extended along a longitudinal axis; an assist tool which is detachably attached to the insertion section, the assist tool being actuated in a state of being attached to the insertion section, thereby causing a propulsion force for movement along the longitudinal axis to act on the insertion section; a moving member which is provided in one of the insertion section and the assist tool, and which is movable between a first position and a second position, wherein: the moving member is located at the first position or between the first position and the second position, in a state in which the assist tool is located at a position different from a specific position relative to the insertion section; and the moving member is located at the second position due to a pressure from the other of the insertion section and the assist tool, in a state in which the assist tool is located at the specific position relative to the insertion section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
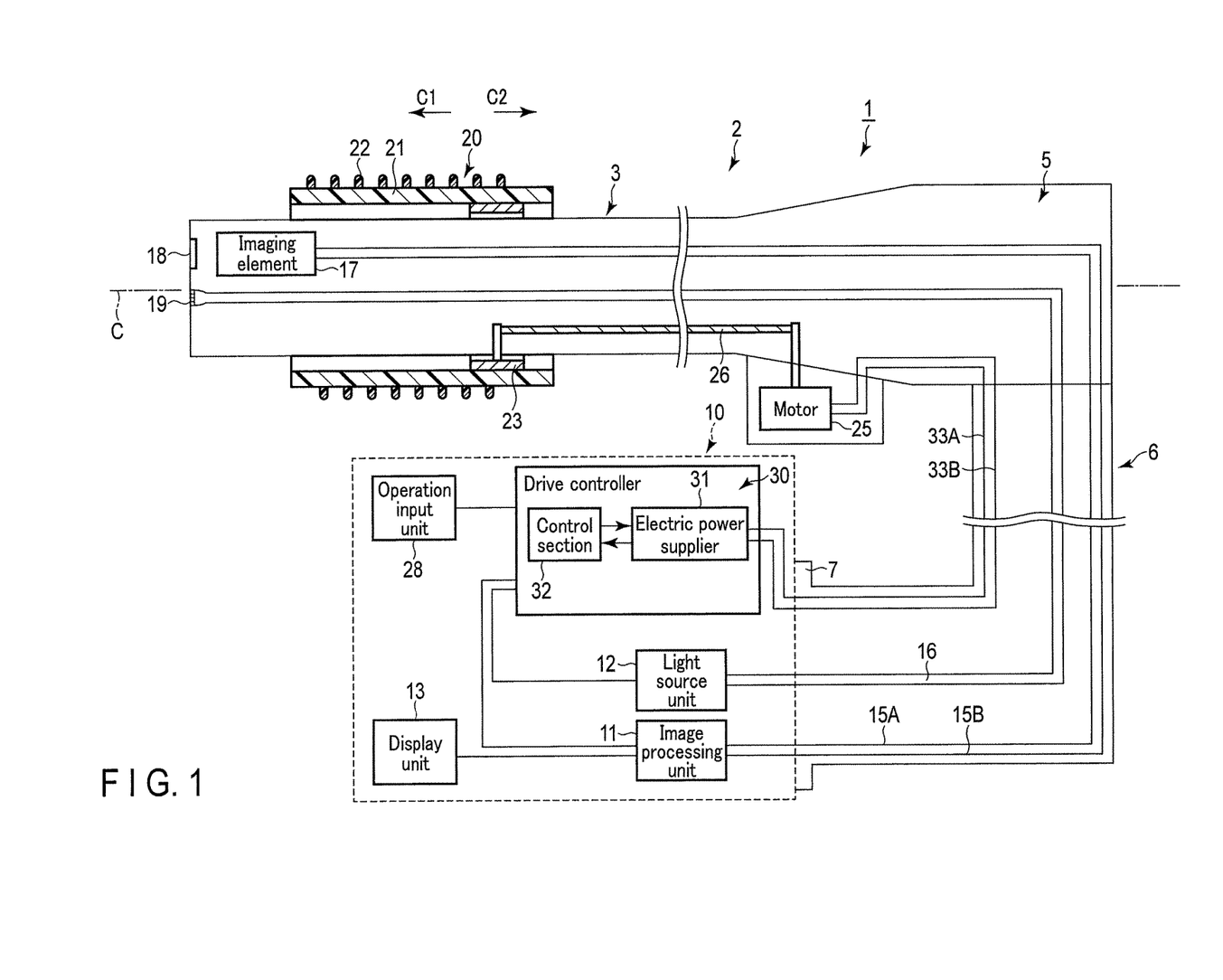
FIG. 1 is a schematic diagram of an endoscope device using an endoscope according to a first embodiment.

The first embodiment of the present invention will be explained with reference to FIG. 1 to FIG. 4. FIG. 1 is a diagram showing an endoscope device (endoscope system) 1, which is an insertion device using an endoscope 2, which is an insertion instrument of this embodiment.

The endoscope 2, which is the insertion instrument, has a longitudinal axis C as shown in FIG. 1. A direction along the longitudinal axis C (parallel to the longitudinal axis C) is defined as a longitudinal axis direction. One side of the longitudinal axial direction is a distal side (a side of an arrow C1 in FIG. 1), and a side opposite to the distal side is a proximal side (a side of an arrow C2 in FIG. 1). The endoscope 2 includes an insertion section (endoscope insertion section) 3 extended along the longitudinal axis C, and an operation section (endoscope operation section) 5 provided on a proximal side with respect to the insertion section. When the endoscope device 1 is used, for example, the insertion section 3 is inserted into a lumen to observe the lumen.

One end of a universal cord 6 is connected to the operation section 5. Another end of the universal cord 6 is provided with a connector 7, and the universal cord 6 is connected to a peripheral unit 10 via the connector 7. In the endoscope device 1, an image processing unit 11, such as an image processor, a light source unit 12 including a light source, such as a lamp, and a display unit 13, such as a monitor, are provided as the peripheral unit 10 of the endoscope 2. In this embodiment, the connector 7 of the universal cord 6 is connected to the light source unit 12.

Furthermore, in the endoscope 2, imaging cables 15A and 15B and a light guide 16 are extended through an inside of the insertion section 3, an inside of the operation section 5, and an inside of the universal cord 6. An imaging element 17, such as a CCD, is provided inside a distal portion of the insertion section 3. The imaging element 17 captures an image of an object through an observation window 18 provided on a distal surface of the insertion section 3. An image signal is transmitted through the imaging cables 15A and 15B to the image processing unit 11, and image processing is carried out in the image processing unit 11. As a result, an image of the object is generated in the image processing unit 11, and the generated image of the object is displayed in the display unit 13. Light emitted from the light source unit 12 is guided through the light guide 16. The guided light is radiated on the object through an illumination window 19 provided on the distal surface of the insertion section 3.

A spiral unit 20 is detachably attached to the insertion section 3 in a state of surrounding an outer periphery of the insertion section 3. The spiral unit 20 is attached to the insertion section 3 in a state in which the insertion section 3 is inserted through the spiral unit 20. The spiral unit 20 includes a tube main body 21, and a fin 22 projecting to an outer side from an outer peripheral surface of the tube main body 21. The fin 22 is spirally extended around the longitudinal axis C on the outer peripheral surface of the tube main body 21.

Furthermore, a cylindrical rotator 23 is attached to the insertion section 3 in a state in which the insertion section 3 is inserted through the rotator. The rotator 23 is rotatable relative to the insertion section 3 around the longitudinal axis C. The spiral unit 20 is attached to the rotator 23 from an outer peripheral side of the rotator 23. Thus, the spiral unit 20 is attached to the insertion section 3 via the rotator 23.

A motor 25, which is a driving source, is attached to the operation section (held section) 5. The motor 25 is rotationally driven upon being supplied with a driving electric power (electric power). The motor 25 is driven, thereby generating a driving force that rotates the spiral unit 20 and the rotator 23. In other words, driving of the motor 25 generates a driving force that actuates the spiral unit (assist tool) 20. A shaft 26 is extended inside the insertion section 3 in the longitudinal axis direction. The driving force generated in the motor 25 is transmitted to the rotator 23 through the shaft 26. The driving force is transmitted to the rotator 23, and thereby the rotator 23 rotates around the longitudinal axis C. As a result, the driving force is transmitted to the spiral unit 20, and the spiral unit 20 rotates relative to the insertion section 3 around the longitudinal axis C.

The spiral unit 20 rotates in a state in which the fin 22 is pressed toward an inner peripheral side by a lumen wall or the like, and thereby a propulsion force toward a distal side or a proximal side acts on the insertion section 3 and the spiral unit 20. In other words, the spiral unit (assist tool) 20 is actuated in a state of being attached to the insertion section 3, thereby causing the propulsion force that moves the insertion section 3 along the longitudinal axis C to act. Mobility (insertion performance) of the insertion section 3 in a lumen or the like toward the distal side is improved by the propulsion force toward the distal side, while mobility (extraction performance) of the insertion section 3 in a lumen or the like toward the proximal side is improved by the propulsion force toward the proximal side.

The peripheral unit 10 includes an operation input unit 28, such as a foot switch, to which an operation to rotate (actuate) the spiral unit 20 is input, and a drive controller 30 that is a control device to control a driving state of the motor 25 based on an operation input in the operation input unit 28. The drive controller 30 includes an electric power supplier 31 that outputs an electric power to be supplied to the motor 25, and a control section 32 that controls the electric power supplier 31 based on an operation input in the operation input unit 28. Electric wires 33A and 33B are extended inside the operation section 5 and inside the universal cord 6. The electric power supplier 31 is connected to the motor 25 through the electric wires 33A and 33B. The electric power supplier 31 includes a power supply, and a converter circuit or the like that converts an electric power from the power supply to a driving electric power to be supplied to the motor 25. The driving electric power output from the electric power supplier 31 is supplied to the motor 25 through the electric wires 33A and 33B, thereby driving the motor 25. Furthermore, the control section 32 includes a processor including a CPU (Central Processing Unit) or an ASIC (Application Specific Integrated Circuit) etc., and a storage, such as a memory. The control section 32 may be formed of one processor or a plurality of processors. The drive controller 30 may be integrated with, for example, the image processing unit 11 that performs image processing.

Figure 2:
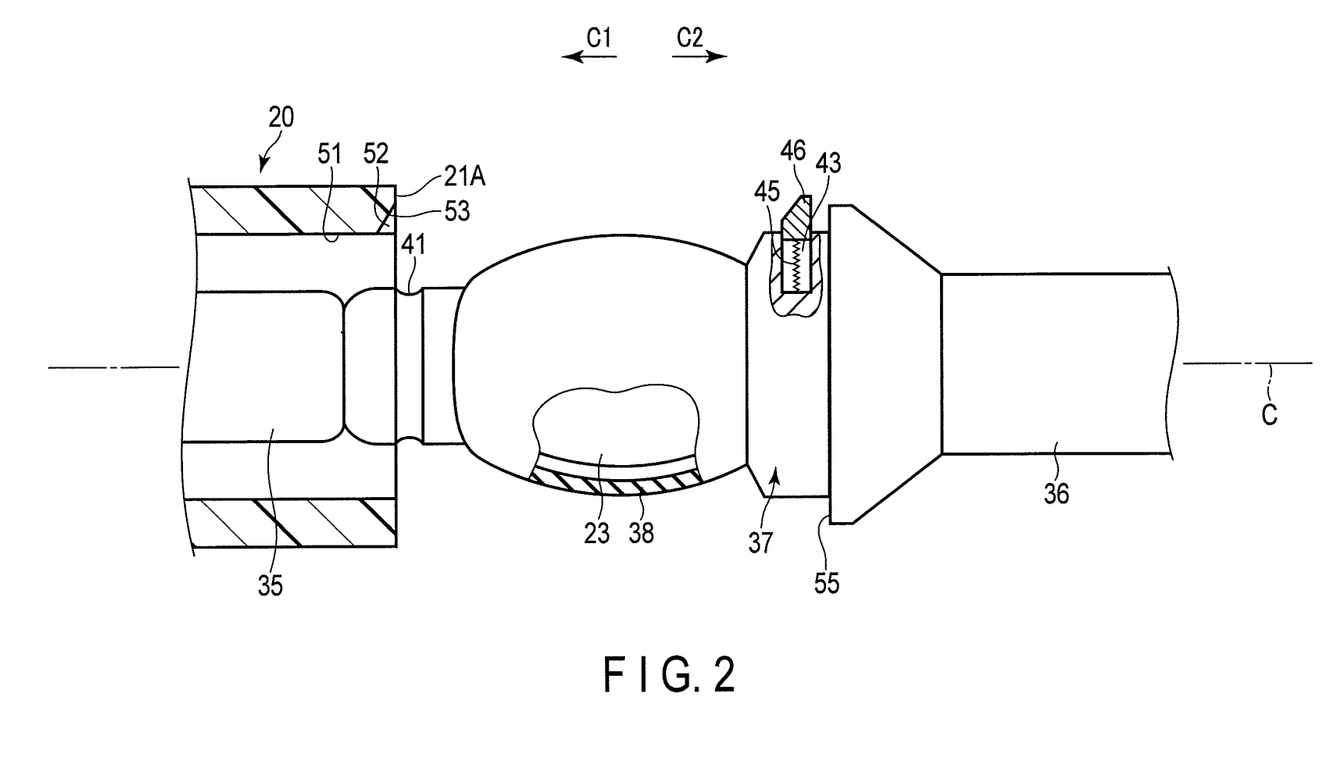
FIG. 2 is a schematic diagram showing a configuration of a proximal portion of a spiral unit, which is an assist tool according to the first embodiment, and a region of an insertion section near a part to which the spiral unit is to be connected, in a state in which the spiral unit is not connected to the insertion section.
Figure 3:
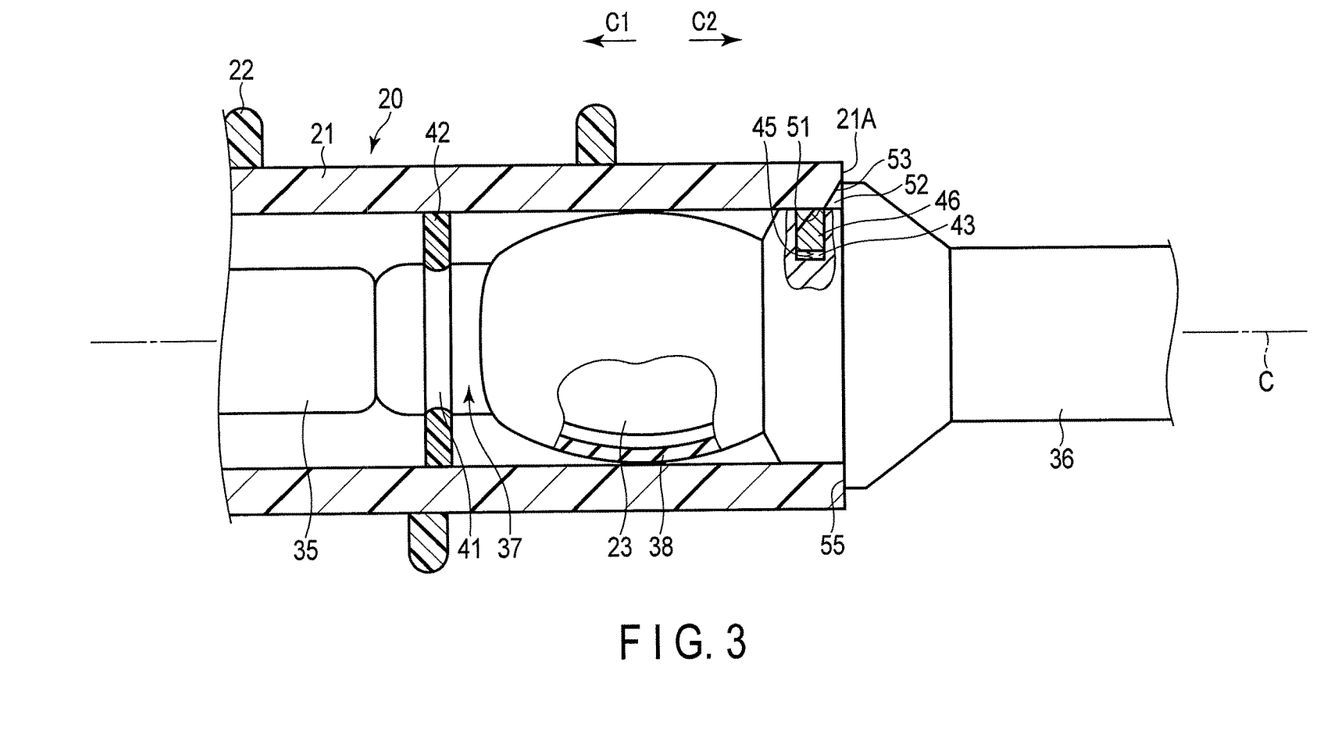
FIG. 3 is a schematic diagram showing a configuration of the proximal portion of the spiral unit according to the first embodiment, and the region of the insertion section near the part to which the spiral unit is to be connected, in a state in which the spiral unit is attached to the insertion section at a specific position.
Figure 4:
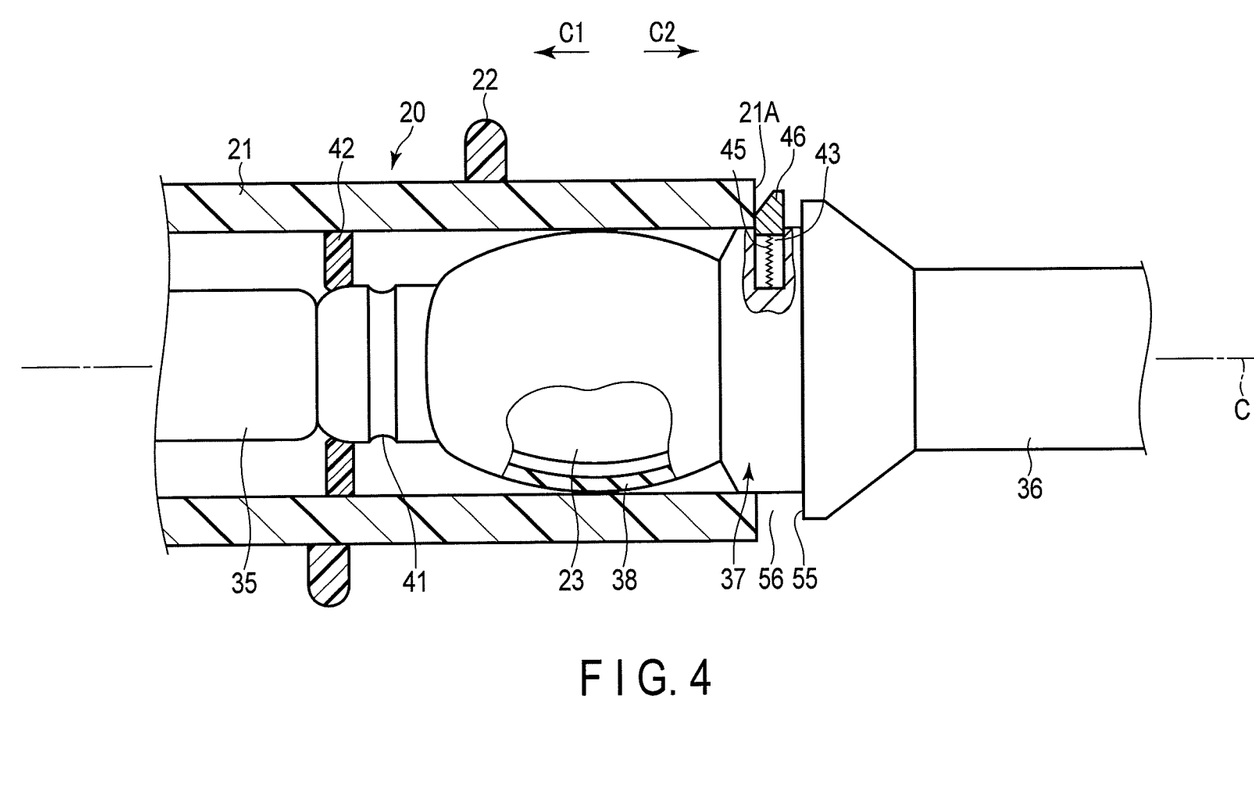
FIG. 4 is a schematic diagram showing a configuration of the proximal portion of the spiral unit according to the first embodiment, and the region of the insertion section near the part to which the spiral unit is to be connected, in a state in which the spiral unit is attached to the insertion section at a position different from the specific position.

FIGS. 2 to 4 are diagrams showing a configuration of the proximal portion of the tube main body 21 and a region of the insertion section 3 near a part to which the spiral unit 20 is to be connected. FIG. 2 shows a state in which the spiral unit 20 is not connected to the insertion section 3. FIG. 3 shows a state in which the spiral unit 20 is attached to the insertion section 3 at a specific position (proper position). FIG. 4 shows a state in which the spiral unit 20 is attached to the insertion section 3 at a position different from the specific position (a position dislocated from the specific position).

As shown in FIG. 2 to FIG. 4, the insertion section 3 includes a distal side flexible tube section 35, and a proximal side flexible tube section 36 provided on a proximal side with respect to the distal side flexible tube section 35. The insertion section 3 also includes a base section 37 that couples the distal side flexible tube section 35 and the proximal side flexible tube section 36. The rotator 23 is connected to the base section 37 to be rotatable relative to the insertion section 3 around the longitudinal axis C. The tube main body 21 of the spiral unit 20, i.e., the assist tool, is coupled to the base section 37 via the rotator 23. In this embodiment, the outer periphery of the rotator 23 is covered with a cover member 38. Thus, the cover member 38 is provided between the rotator 23 and the spiral unit 20 in radial direction. A distal end and a proximal end of the cover member 38 are fixed to the base section 37. While the cover member 38 is provided, in the state in which the spiral unit 20 is attached to the insertion section 3, the rotator 23 is rotated, and thereby a driving force is transmitted to the spiral unit 20 and the spiral unit 20 rotates.

An engagement groove 41 is provided over a whole circumference of an outer peripheral surface of the base section 37 around the longitudinal axis C in a part located on a distal side with respect to the rotator body 23 and the cover member 38. On the other hand, an engagement projection 42 engageable with the engagement groove 41 is formed on an inner peripheral surface of the tube main body 21. The engagement projection 42 is preferably made of, for example, a synthetic resin material. In the state (the state of FIG. 3) in which the spiral unit 20 is attached to the insertion section 3 at the specific position (proper position), the engagement projection 42 engages with the engagement groove 41. In this state, as the spiral unit 20 rotates relative to the insertion section 3, the engagement projection 42 slides around the longitudinal axis C within the engagement groove 41. Engagement of the engagement projection 42 with the engagement groove 41 restricts movement of the spiral unit 20 relative to the insertion section 3 in the longitudinal axial direction. In the state (the state of FIG. 4) in which the spiral unit 20 is attached to the insertion section 3 at a position different from the specific position (a position dislocated from the specific position), the engagement projection 42 does not engage with the engagement groove 41. Even in the state in which the spiral unit 20 is attached to the insertion section 3 at a position different from the specific position, the spiral unit 20 is connected to an outer peripheral side of the rotator body 23. Therefore, the rotator body 23 may rotate, and a driving force may be transmitted to the spiral unit 20 and the spiral unit 20 may rotate (actuate).

A recess 43 is provided on the outer peripheral surface of the base section 37. In this embodiment, the recess 43 is located on a proximal side with respect to the rotator 23. In the recess 43, a moving member 46 is attached to the base section 37 via an urging member (elastic member) 45. The moving member 46 is movable between a first position, i.e., a projecting position (a position shown in FIG. 2 and FIG. 4) where the moving member projects out of an outer periphery of the base section 37 by an urging force of the urging member 45 and a second position, i.e., a retracted position (a position shown in FIG. 3) where the moving member is retracted inside the recess 43 against the urging force of the urging member 45.

The inner peripheral surface of the proximal portion of the tube main body 21 in the spiral unit 20 is provided with a pressing section (pressing surface) 51 that exerts a pressure on the moving member 46 toward an inner peripheral side in the state (the state of FIG. 3) in which the spiral unit 20 is attached to the insertion section 3 at the specific position. The moving member 46 is held in the retracted position by the pressure from the pressing section 51 against the urging force from the urging member 45. Thus, the pressing section 51 is provided in a proximal-side-part of the inner peripheral surface of the spiral unit (assist tool) 20 and is abutable with the moving member 46. The moving member 46 moves to the retracted position (second position) by the abutment of the pressing section 51.

Furthermore, in the tube main body 21, a guide groove 52 is formed obliquely from a proximal surface 21A to the inner peripheral surface, and a bottom of the guide groove 52 is defined as a groove defining surface 53. In this embodiment, the groove defining surface 53 is continuous to a proximal side of the pressing section 51. In the groove defining surface 53, a distance from the longitudinal axis C (the rotation axis of the spiral unit 20) reduces from the proximal side toward the distal side. When the spiral unit 20 is attached to the insertion section 3 at the specific position (proper position), the guide groove 52 passes by the moving member 46 attached to the base section 37 from the proximal end thereof toward the proximal side. When the guide groove 52 passes by the moving member 46, the groove defining surface 53, which is a pressure applying surface, applies a pressure to the moving member 46 toward an inner peripheral side. Accordingly, the moving member 46 moves from the projecting position to the retracted position against the urging force from the urging member 45. Passing of the distal end of the guide groove 52 by the moving member 46 toward the proximal side causes the spiral unit 20 to be attached to the insertion section 3 at the specific position (proper position). When the distal end of the guide groove 52 passes by the moving member 46 toward the proximal side, the pressing section 51 presses the moving member 46 toward an inner side and holds the moving member 46 in the retracted position (second position).

Furthermore, the base section 37 is provided with an abutment surface 55, to which the proximal surface 21A of the tube main body 21 abuts in the state in which the spiral unit 20 is attached to the insertion section 3 at the specific position (the state of FIG. 3). In other words, the proximal surface 21A of the tube main body 21 abuts the abutment surface 55 of the base section 37, in the state in which the moving member 46 is in the retracted position due to the pressure from the pressing section 51. As a result of this abutment motion, no gap is left between the proximal surface 21A and the abutment surface 55. In this embodiment, the abutment surface 55 is located on the proximal side with respect to the recess 43 and faces to the distal side.

In the state (the state of FIG. 4) in which the spiral unit 20 is attached to the insertion section 3 at a position different from the specific position (a position dislocated from the specific position), the moving member 46 is located in the projecting position (first position) or between the projecting position and the second position (an intermediate position), and the proximal end of the spiral unit 20 is located on the distal side with respect to the moving member 46. For example, assume that the spiral unit 20 is moved relative to the insertion section 3 toward the proximal side to attach the spiral unit 20 to the insertion section 3, in a state in which an angular position of the guide groove 52 is displaced from the moving member 46 in a direction around the longitudinal axis C. In this case, since the angular position of the guide groove 52 is deviated from the moving member 46 in the direction around the longitudinal axis C, the moving member 46 is not pressed by the pressing section 51 and the groove defining surface 53, which is a pressure applying surface, but is maintained in the projecting position by an urging force from the urging member 45. Therefore, even when the spiral unit 20 is moved relative to the insertion section 3 toward the proximal side, the proximal surface 21A of the tube main body 21 is brought into abutment with the moving member 46 at the projecting position. As a result, movement of the spiral unit 20 toward the proximal side is restricted.

In other words, in the state (the state of FIG. 4) in which the spiral unit 20 is attached to the insertion section 3 at a position different from the specific position (a position dislocated from the specific position), the moving member 46 is located in the projecting position. Accordingly, the proximal surface 21A of the tube main body 21 does not move toward the proximal side over the moving member 46, but is located on the distal side with respect to the moving member 46. Since the proximal surface 21A of the tube main body 21 is located on the distal side with respect to the moving member 46, there is a gap 56 between the proximal surface 21A and the abutment surface 55, in the state in which the spiral unit 20 is attached to the insertion section 3 at a position different from the specific position.

Even when the angular position of the guide groove 52 coincides with the moving member 46 in the direction around the longitudinal axis C, in a state in which the spiral unit 20 has not moved to the specific position relative to the insertion section 3 toward the proximal side, the moving member 46 is maintained at the projecting position or at an intermediate position between the projecting position and the retracted position, and is not retracted in the retracted position. Therefore, a gap 56 is left between the proximal surface 21A and the abutment surface 55.

As described above, the moving member 46 is in the retracted position by the pressure from the pressing section 51 and the spiral unit 20 is in abutment with the abutment surface 55, only in the state (the state of FIG. 3) in which the spiral unit 20 is attached to the insertion section 3 at the specific position (proper position). In the state (the state of FIG. 4) in which the spiral unit 20 is attached to the insertion section 3 at a position different from the specific position (a position dislocated from the specific position), the moving member 46 is located in the projecting position or between the projecting position and the retracted position, and there is a gap 56 between the proximal surface 21A and the abutment surface 55. Therefore, the gap 56 serves as a kind of index that is visible and indicates whether or not the spiral unit (assist tool) 20 is located at the specific position relative to the insertion section 3. The moving member 46 also serves as a kind of index indicating whether or not the spiral unit (assist tool) 20 is located at the specific position relative to the insertion section 3.

Next, functions and advantageous effects of the endoscope device (endoscope system) 1, which is the insertion device of this embodiment, are described. When a lumen is observed by using the endoscope device 1, the spiral unit 20, which is the assist tool, is attached to the insertion section 3, and the insertion section 3 and the spiral unit 20 are inserted into the lumen. Thus, the spiral unit 20 is actuated in accordance with an input operation in the operation input unit 28. When the spiral unit 20 is actuated, the spiral unit 20 and the rotator 23 rotate relative to the insertion section 3 around the longitudinal axis C. The spiral unit 20 rotates in a state in which the fin 22 is pressed by a lumen wall, and thereby a propulsion force acts on the insertion section 3 and the spiral unit 20 toward one side in the longitudinal axis direction. Mobility of the insertion section 3 in the lumen is improved by the propulsion force.

In this embodiment, a pressure acts on the moving member 46 from the groove defining surface 53 and the pressing section 51 toward an inner peripheral side, only in the case in which the spiral unit 20 is attached to the insertion section 3 at the specific position (for example, the position where the engagement projection 42 properly engages with the engagement groove 41). Thus, by the pressure from the groove defining surface 53 and the pressing section (pressing surface) 51, the moving member 46 moves from the projecting position (first position) to the retracted position (second position), and is held in the retracted position. Since the state in which the moving member 46 is in the retracted position, the proximal surface 21A of the tube main body 21 contacts the abutment surface 55.

On the other hand, in the state in which the spiral unit 20 is attached to the insertion section 3 at a position different from the specific position, the moving member 46 is not pressed by the pressing section 51 or the proximal surface 21A of the tube main body 21. Accordingly, the moving member 46 is in the projecting position. Therefore, the proximal surface 21A of the tube main body 21 is located on the distal side with respect to the moving member 46, and there is a gap 56 between the proximal surface 21A and the abutment surface 55.

An operator properly recognizes that the spiral unit 20 is attached to the insertion section 3 at the specific position (proper position) based on whether or not there is a gap 56 between the proximal surface 21A of the tube main body 21 and the abutment surface 55. The operator can also recognize whether or not the spiral unit 20 is attached to the insertion section 3 at the specific position (proper position) based on the position of the moving member 46 (whether or not the moving member is at the retracted position). As a result, it is possible to effectively prevent the spiral unit 20 from being actuated (actuated in an erroneous attachment state) in a state in which the spiral unit 20 is not at the specific position relative to the insertion section 3 (that is, a state in which the spiral unit 20 is not properly attached to the insertion section 3). Since the spiral unit 20 is prevented from being actuated in a state in which the spiral unit 20 is not at the specific position relative to the insertion section 3, it is possible to effectively prevent a malfunction in the endoscope device 1 or detachment of the spiral unit 20 from the insertion section 3 during observation of a lumen. Even if the moving member 46 is not provided, if there is no gap 56 between the proximal surface 21A of the tube main body 21 and the abutment surface 55, the surgeon can properly recognize that the spiral unit 20 is attached to the insertion section 3 at the specific position (proper position).

Modification of First Embodiment

In the first embodiment, only one moving member 46 is provided; however, the number of moving members is not limited. For example, a plurality of moving members 46 may be provided with intervals therebetween around the longitudinal axis C.

Figure 5:
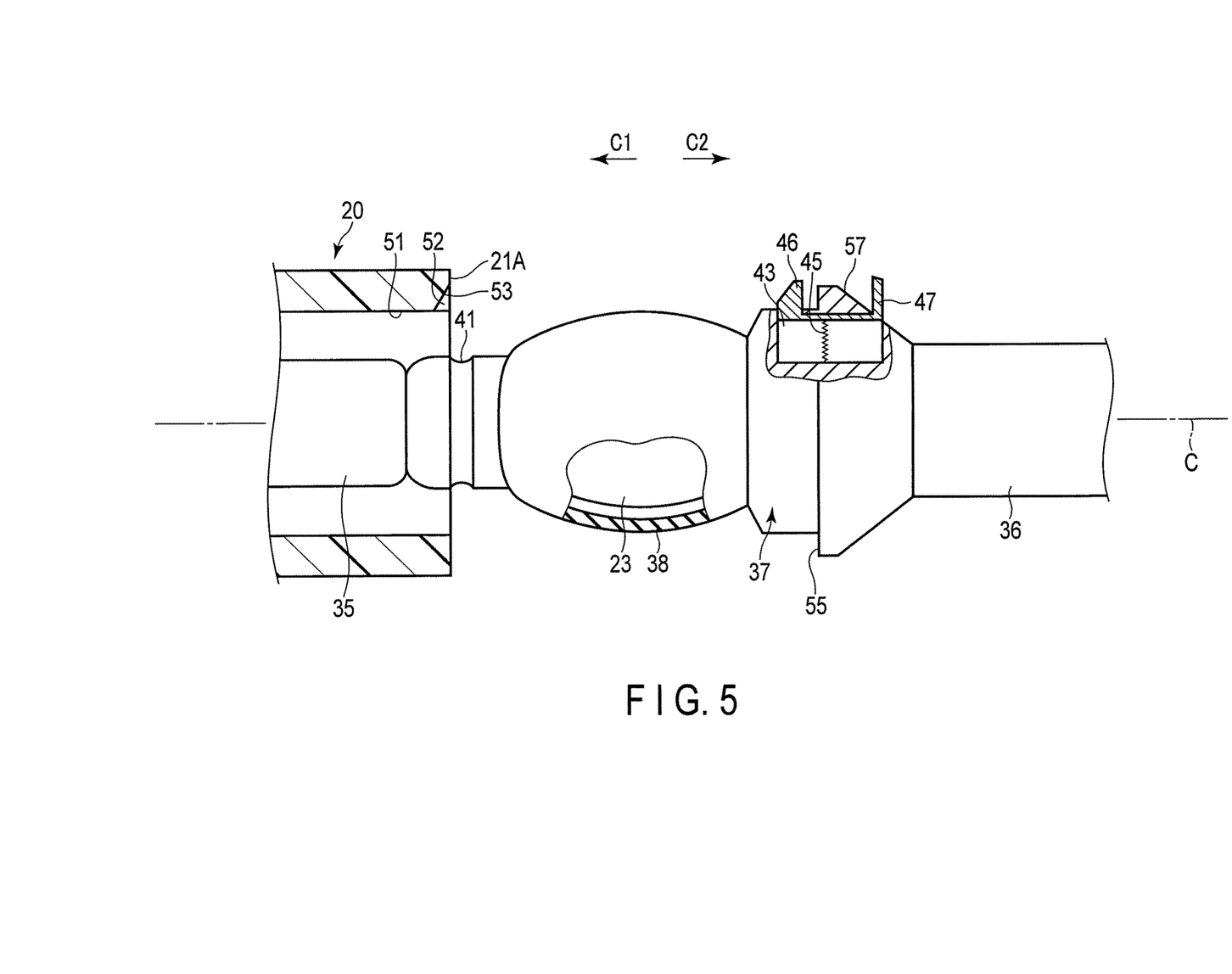
FIG. 5 is a schematic diagram showing a configuration of a proximal portion of a spiral unit according to a modification of the first embodiment, and a region of an insertion section near a part to which the spiral unit is to be connected, in a state in which the spiral unit is not connected to the insertion section.

In the modification of the first embodiment shown in FIG. 5, a base of the moving member 46 is extended to a part located on the proximal side with respect to the abutment surface 55. Moreover, a tapered conical surface 57 is formed on the outer peripheral surface of the insertion section 3 on the proximal side of the contact surface 55. In a state in which the moving member 46 is in the projecting position, an outer peripheral end of a proximal portion 47 of the base of the moving member 46 projects outside the conical surface 57. On the other hand, in a state in which the moving member 46 is at the retracted position, the outer peripheral end of the proximal portion 47 of the base of the moving member 46 is located on the same plane with the conical surface 57. With the configuration described above, in the state in which the spiral unit 20 is attached to the insertion section 3 at a specific position (proper position), the proximal portion 47 of the base of the moving member 46 is retracted inside the conical surface 57. Therefore, the operator can visually and easily determine whether or not the spiral unit 20 is at the specific position.

Second Embodiment

The second embodiment of the present invention will be explained with reference to FIG. 6 to FIG. 9. The second embodiment is a modification of the configuration of the first embodiment as described below. In the following, parts identical to those of the first embodiment will be assigned identical symbols, and explanations thereof will be omitted.

Figure 6:
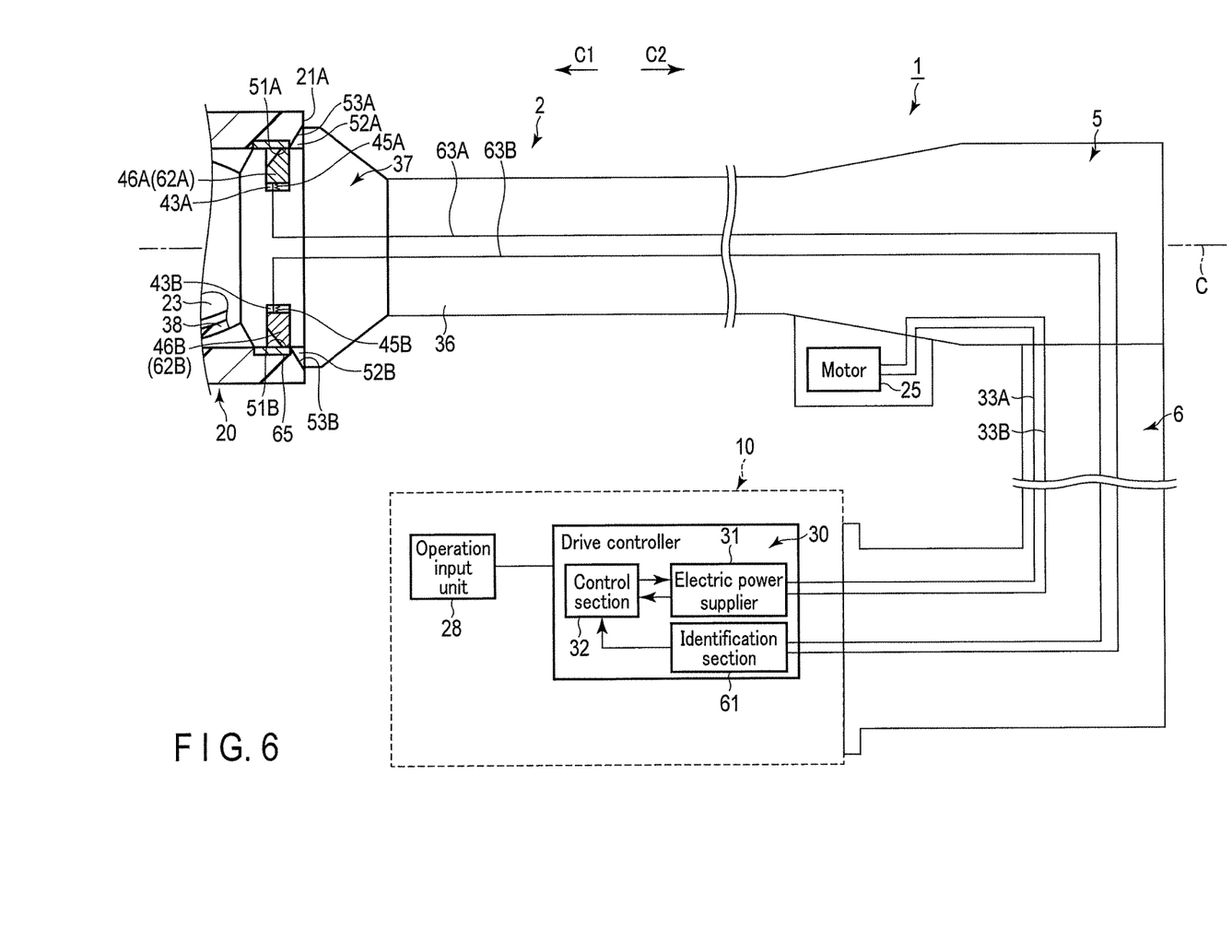
FIG. 6 is a schematic diagram of an endoscope device using an endoscope according to a second embodiment.

FIG. 6 is a diagram showing an endoscope device (endoscope system) 1 that is an insertion device using an endoscope 2, which is an insertion instrument of this embodiment. In FIG. 6, an image processing unit 11, a light source unit 12, a display unit 13, imaging cables 15A and 15B, a light guide 16, and a shaft 26 are omitted. In this embodiment, a spiral unit 20 is attached to a base section 37 of an insertion section 3 via a rotator 23, in the same manner as in the first embodiment. As shown in FIG. 6, an operation section 5 is provided with a motor 25, which is a driving source. A drive controller 30 includes an electric power supplier 31 and a control section 32. A driving electric power is supplied from the electric power supplier 31 to the motor 25, thereby generating a driving force in the motor 25. The driving force is transmitted to the spiral unit 20 through the shaft 26 and the rotator 23, and the spiral unit 20 is actuated.

Furthermore, in this embodiment, moving members 46A and 46B are attached to the base section 37. In this embodiment, the moving members 46A and 46B are located at angular positions spaced at about 180 degrees relative to each other around the longitudinal axis C. As in the case of the moving member 46 of the first embodiment, each of the moving members 46A and 46B is attached to the base section 37 via a corresponding urging member (45A or 45B) in a corresponding recess (43A or 43B). Each of the moving members 46A and 46B is movable between a projecting position (first position) and a retracted position (second position). In this embodiment, as well as the first embodiment, each of the moving members 46A and 46B moves from the projecting position to the retracted position, and is held in the retracted position by a corresponding pressing section (51A or 51B), only in the state in which the spiral unit 20 is attached to the insertion section 3 at a specific position (proper position). Therefore, a proximal surface 21A of the tube main body 21 abuts an abutment surface 55, in the state in which the spiral unit 20 is attached to the insertion section 3 at the specific position (proper position). Furthermore, each of groove defining surfaces 53A and 53B defines a corresponding guide groove (52A or 52B) on a proximal side of a corresponding pressing section (51A or 51B).

Also in this embodiment, in the state in which the spiral unit 20 is attached to the insertion section 3 at a position different from the specific position (a position dislocated from the specific position), each of the moving members 46A and 46B does not move from the projecting position to the retracted position, and the proximal surface 21A of the tube main body 21 is located on the distal side with respect to the moving members 46A and 46B. Therefore, in the state in which the spiral unit 20 is attached to the insertion section 3 at a position different from the specific position, there is a gap 56 between the proximal surface 21A and the abutment surface 55.

In this embodiment, the drive controller 30 includes an identification section 61. The identification section 61 is formed of, for example, an electronic circuit (integrated circuit) of a processor provided in a control section 32, or an electronic circuit (integrated circuit) independent of the processor provided in the control section 32. The identification section 61 identifies whether or not the spiral unit 20, which is an assist tool, is attached to the insertion section 3 at the specific position (proper position). Therefore, in this embodiment, the control section 32 controls an output state (a supply state) of a driving electric power from the electric power supplier 31 based on an identification result in the identification section 61 in addition to an operation input in the operation input unit 28.

Furthermore, in this embodiment, a first electric contact 62A is provided on the moving member 46A, and a second electric contact 62B is provided on the moving member 46B. In this embodiment, the first electric contact 62A and the second electric contact 62B are exposed on an outer surface of the insertion section 3. Electric paths 63A and 63B are extended inside the insertion section 3, inside the operation section 5, and inside the universal cord 6. The first electric contact 62A is connected to the identification section 61 through the electric path (first electric path) 63A. The second electric contact 62B is connected to the identification section 61 through the electric path (second electric path) 63B. The identification section 61 outputs an electric power as a sensing signal through the electric paths 63A and 63B.

Figure 7:
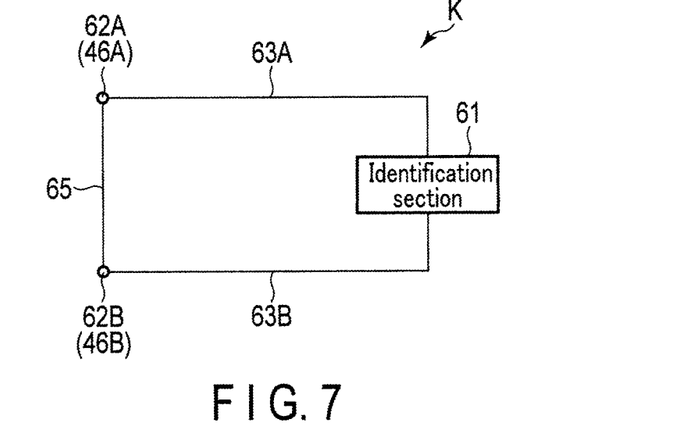
FIG. 7 is a schematic diagram showing a configuration of a sensing circuit to which a sensing signal from an identification section is output, in a state in which a spiral unit according to the second embodiment is attached to an insertion section at a specific position.
Figure 8:
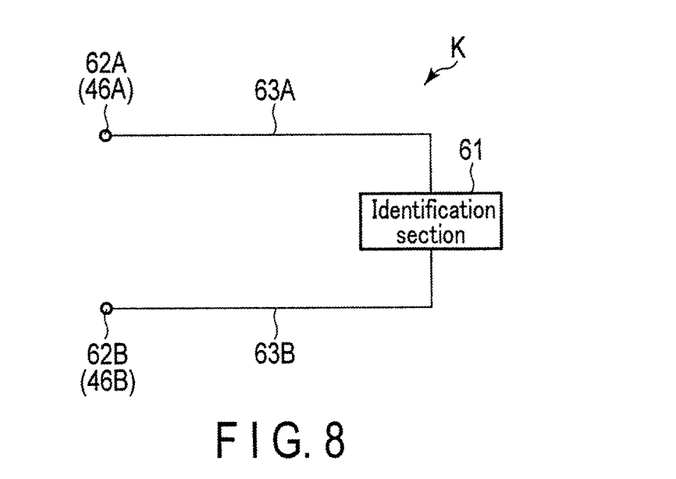
FIG. 8 is a schematic diagram showing a configuration of the sensing circuit to which the sensing signal from the identification section is output, in a state in which the spiral unit according to the second embodiment is attached to the insertion section at a position different from the specific position.

FIG. 7 and FIG. 8 are diagrams showing configurations of a sensing circuit K in which a sensing signal is output from the identification section 61. FIG. 7 shows a state in which the spiral unit 20, which is the assist tool, is attached to the insertion section 3 at a specific position (proper position). FIG. 8 shows a state in which the spiral unit 20 is attached to the insertion section 3 at a position different from the specific position (a position dislocated from the specific position). As shown in FIG. 6 to FIG. 8, the spiral unit 20 is provided with, for example, a cylindrical conductive section 65 as an identified element. In this embodiment, pressing sections 51A and 51B are formed by an inner peripheral surface of the conductive section 65.

When each of the moving members 46A and 46B is located in the retracted position by a pressure from the corresponding pressing section (51A or 51B), as shown in FIG. 7, the conductive section 65 is brought into electrical contact with the first electric contact 62A and the second electric contact 62B from an outer peripheral side. As the conductive section 65 contacts the first electric contact 62A and the second electric contact 62B, the first electric contact 62A and the second electric contact 62B are electrically connected to each other through the conductive section 65. In other words, by attachment of the spiral unit (assist tool) 20 to the insertion section 3 at the specific position (proper position), the conductive section 65 electrically connects the first electric contact 62A and the second electric contact 62B. Accordingly, when a sensing signal is output from the identification section 61, a current flows between the first electric contact 62A and the second electric contact 62B through the conductive section 65.

On the other hand, in a state in which the moving members 46A and 46B are in the projecting position or between the projecting position and the retracted position (an intermediate position), the conductive section 65 does not contact the first electric contact 62A and the second electric contact 62B, and the second electric contact 62B is electrically insulated from the first electric contact 62A, as shown in FIG. 8. Therefore, no current flows between the first electric contact 62A and the second electric contact 62B. In other words, in the state in which the spiral unit 20 is attached to the insertion section 3 at a position different from the specific position (a position dislocated from the proper position), the second electric contact 62B is electrically insulated from the first electric contact 62A and no current flows between these contacts.

In this embodiment, whether or not a current flows between the first electric contact 62A and the second electric contact 62B depends on whether or not the moving members 46A and 46B are located in the retracted positions, that is, whether the spiral unit 20 is attached to the insertion section 3 at the specific position. In other words, by attachment of the spiral unit 20 to the insertion section 3 at the specific position (proper position), a current flowing between the first electric contact 62A and the second electric contact 62B (a physical quantity) changes due to the conductive section 65, which is an identified element. By provision of the first electric contact 62A and the second electric contact 62B as sensing sections in the insertion section 3, a change in current flowing between the first electric contact 62A and the second electric contact 62B due to the conductive section 65 is sensed. Therefore, movement of the moving members 46A and 46B to the retracted positions is sensed by the first electric contact 62A and the second electric contact 62B. Based on a sensing result of the current (the physical quantity) that changes due to the conductive section (identified element) 65, the identification section 61 determines whether or not the spiral unit 20, which is the assist tool, is located at the specific position (proper position) relative to the insertion section 3. In other words, based on the sensing result of the current flowing between the first electric contact 62A and the second electric contact 62B, a position of the spiral unit 20 relative to the insertion section 3 is identified. Only in a case in which the identification section 61 determines that the spiral unit 20 is located at the specific position relative to the insertion section 3, the control section 32 controls the electric power supplier 31, so that a driving electric power can be supplied to the motor (driving source) 25. Two electric contacts spaced apart from each other may be disposed near a bottom surface of the recess 43, while the moving member 46 may be formed of a conductive material. In this case, when the moving member 46 is moved to the retracted position in the recess 43 and brought into contact with the two electric contacts, the two electric contacts are short-circuited and the movement of the moving member 46 in the retracted position is sensed.

Next, functions and advantageous effects of the endoscope device (endoscope system) 1, which is the insertion device of this embodiment, are described. In this embodiment, in the same manner as in the first embodiment, when an electric power is supplied from the electric power supplier 31 to the motor 25, the motor 25 is driven, and the driving force is transmitted to the spiral unit 20. Accordingly, the spiral unit 20 is actuated, and rotated in a state in which the fin 22 is pressed by a lumen wall, and thereby a propulsion force acts on the insertion section 3 and the spiral unit 20 in one side of in the longitudinal axis direction. In this embodiment, however, the control section 32 controls electric power supply to the motor 25 and controls an actuation state of the spiral unit 20, based on an identification result in the identification section 61 in addition to the operation input in the operation input unit 28.

Figure 9:
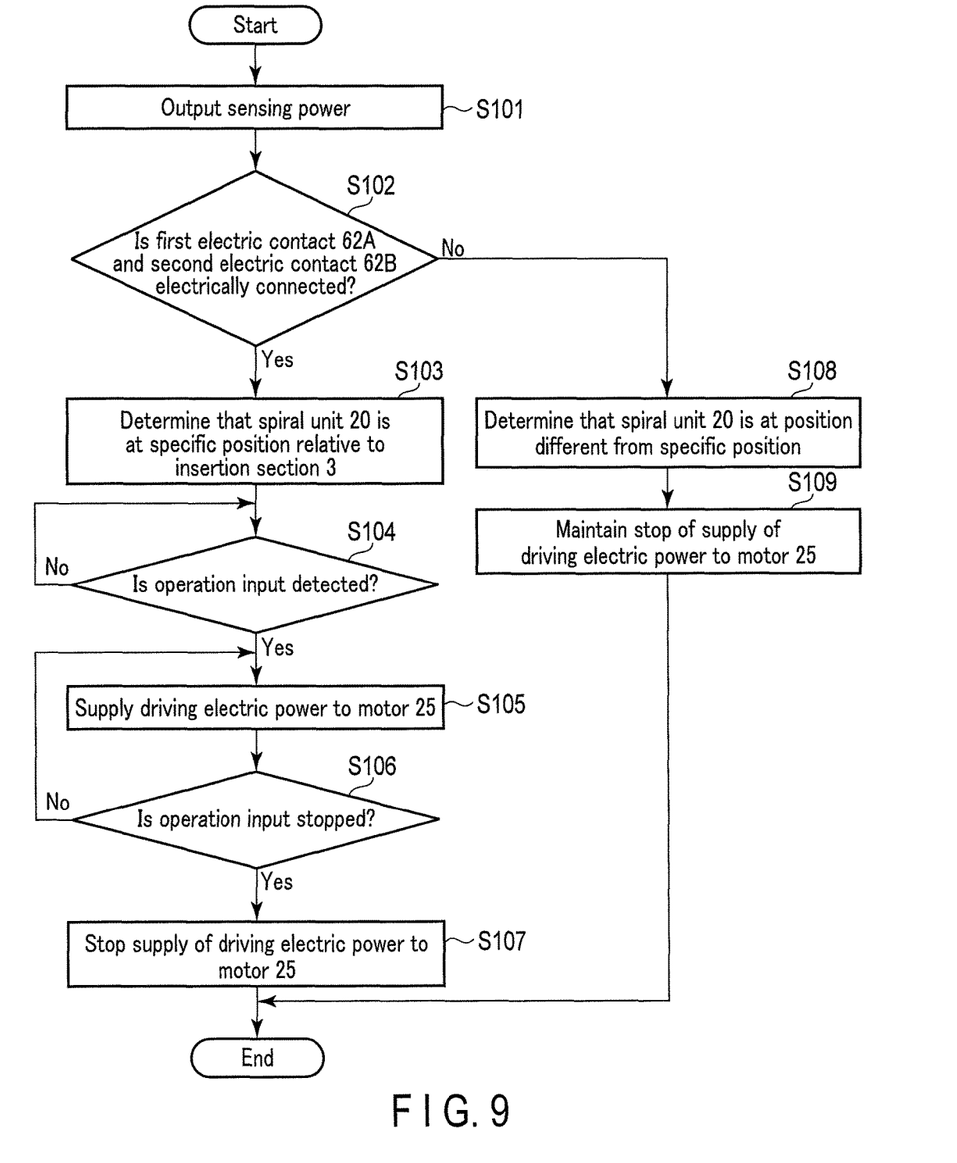
FIG. 9 is a flow chart showing a processing carried out by a drive controller when a motor according to the second embodiment is driven.

FIG. 9 is a flow chart showing a processing carried out by the drive controller 30 when a motor 25, which is a driving source, is driven (when the spiral unit 20 is actuated). As shown in FIG. 9, when the motor 25 is driven, the identification section 61 first outputs a sensing signal to the sensing circuit K (step S101). In the sensing circuit K, a current flowing between the first electric contact 62A and the second electric contact 62B is sensed. The identification section 61 determines whether or not the first electric contact 62A is electrically connected to the second electric contact 62B based on the sensing result of the current flowing between the first electric contact 62A and the second electric contact 62B (step S102).

When the moving members 46A and 46B are located in the retracted positions, that is, in the state in which the spiral unit 20 is attached to the insertion section 3 at the specific position (proper position), the first electric contact 62A and the second electric contact 62B are electrically connected through the conductive section (identified element) 65. Therefore, the identification section 61 determines that the first electric contact 62A and the second electric contact 62B are electrically connected (step S102—Yes). Based on the determination result of step S102, the identification section 61 determines that the moving members 46A and 46B are located at the retracted position and that the spiral unit 20 is at the specific position relative to the insertion section 3 (step S103).

As the determination in step S103 is made, when an operation input is carried out in the operation input unit 28 (step S104—Yes), the control section 32 controls the electric power supplier 31, and a driving electric power is supplied from the electric power supplier 31 to the motor (driving source) 25 (step S105). As long as an operation input continues (step S106—No), the driving electric power is continuously supplied to the motor 25. Supply of the driving electric power to the motor 25 causes the driving force to be transmitted to the spiral unit 20, and the spiral unit 20 is actuated. Accordingly, as described above, a propulsion force acts on the insertion section 3 and the spiral unit 20 in one side of the longitudinal axial direction. When the operation input in the operation input unit 28 is stopped (step S106—Yes), supply of the driving electric power to the motor 25 is stopped (step S107) and the spiral unit 20 stops actuating (rotating).

When the moving members 46A and 46B are located at the projecting position or at an intermediate position between the projecting position and the retracted position, that is, in the state in which the spiral unit 20 is attached to the insertion section 3 at a position different from the specific position (a position dislocated from the proper position), the first electric contact 62A and the second electric contact 62B are electrically insulated from each other. Therefore, the identification section 61 determines that the first electric contact 62A and the second electric contact 62B are not electrically connected (step S102—No). Based on the determination result of step S102, the identification section 61 determines that the moving members 46A and 46B are located at the projecting position or at an intermediate position between the projecting position and the retracted position and that the spiral unit 20 is at a position different from the specific position (step S108). In other words, in step S108, the spiral unit (assist tool) 2 is determined (identified) to be in a state different from the state of being attached to the insertion section 3 at the specific position.

As the determination in step S108 is made, regardless of whether or not there is an operation input in the operation input unit 28, the control section 32 controls the electric power supplier 31 and stop of supply of the driving electric power from the electric power supplier 31 to the motor (driving source) 25 is maintained (step S109). Therefore, in a state in which the spiral unit 20 is attached to the insertion section 3 at a position different from the specific position (proper position), even if an operation input is carried out, the motor 25 is not driven and the spiral unit 20 is not actuated.

The peripheral unit 10 may include an alert unit, such as a lamp, a buzzer, and a display. In this case, an alert may be issued in step S109, instead of maintaining the stop of supplying the driving power to the motor 25, or in addition to maintaining the stop of supplying the driving power to the motor 25.

In this embodiment, as well as the first embodiment, the operator properly recognizes that the spiral unit 20 is attached to the insertion section 3 at the specific position (proper position), based on the position of the moving members 46A and 46B (at which of the projecting position and the retracted position the moving members are located). Furthermore, the operator properly recognizes that the spiral unit 20 is attached to the insertion section 3 at the specific position (proper position) based on whether there is a gap 56 between the spiral unit 20 and the abutment surface 55. Accordingly, it is possible to effectively prevent the spiral unit 20 from being actuated in a state in which the spiral unit 20 is not located at the specific position relative to the insertion section 3 (that is, in a state in which the spiral unit 20 is not properly attached to the insertion section 3).

Moreover, in this embodiment, by attachment of the spiral unit 20 to the insertion section 3 at the specific position (proper position), the first electric contact 62A and the second electric contact 62B are electrically connected through the conductive section 65, and a current (a physical value) flowing between the first electric contact 62A and the second electric contact 62B changes. Thus, the identification section 61 properly determines whether or not the insertion section 3 is attached to the spiral unit 20 at the specific position. Therefore, it is possible to more effectively prevent the spiral unit 20 from being actuated in a state in which the spiral unit 20 is attached to the insertion section 3 at a position different from the specific position (that is, in an erroneous attachment state).

Furthermore, in this embodiment, the control section 32 controls the electric power supplier 31, thereby stopping supply of the driving power to the motor 25, in the state in which the spiral unit 20 is attached to the insertion section 3 at a position different from the specific position. Accordingly, the motor 25 is not driven and no driving force is transmitted to the spiral unit 20 attached to the insertion section 3 at a position different from the specific position. Therefore, it is possible to more effectively prevent the spiral unit 20 from being actuated in a state in which the spiral unit 20 is attached to the insertion section 3 at a position different from the specific position.

Modifications of Second Embodiment

Figure 10:
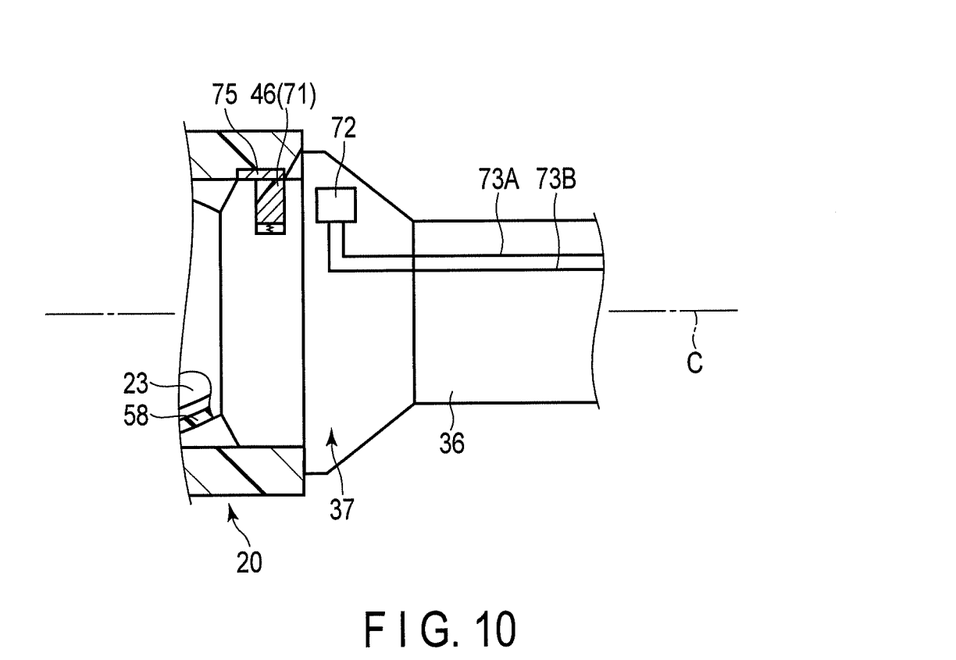
FIG. 10 is a schematic diagram showing a configuration of a proximal portion of a spiral unit according to a first modification of the second embodiment and a region of an insertion section near a moving member, in a state in which the spiral unit is attached to the insertion section at a specific position.

In a first modification of the second embodiment shown in FIG. 10, a moving member 46 is provided in an insertion section 3, and a magnet (insertion section side magnet) 71 is provided in the moving member 46. In the insertion section 3, a magnetic sensor 72 as a sensing section is provided near the moving member 46. The magnetic sensor 72 is electrically connected to an identification section 61 through electric wires 73A and 73B. A spiral unit 20, as an assist tool, is provided with a magnet (attachment side magnet) 75 as an identified element. In this modification, as the moving member 46 moves to a retracted position and the spiral unit 20 is attached to the insertion section at a specific position (proper position), the magnet (attachment side magnet) 75 is brought into contact with the magnet (insertion side magnet) 71. Accordingly, a magnetic field is generated by the magnet 75 and the magnet 71, and a magnetic force of a predetermined range of magnitude acts on the magnetic sensor 72. Based on the magnetic force that acts on the magnetic sensor 72, the identification section 61 identifies whether the spiral unit 20 is attached to the insertion section 3 at the specific position (proper position).

Specifically, in step S102 in FIG. 9, the identification section 61 determines whether the magnetic force acting on the magnetic sensor 72 is in a predetermined range of magnitude or not. If the magnetic force is in the predetermined range of magnitude, it is determined that the spiral unit 20 is attached to the insertion section 3 at the specific position in step S103.

In this modification, since the magnetic sensor 72 is provided in the insertion section 3 as a sensing section, a change in magnetic force acting on the magnetic sensor 72 due to the magnet (attachment side magnet) 75 is sensed. Based on a sensing result of the magnetic force (physical quantity) that changes due to the magnet (identified element) 75, the identification section 61 determines whether or not the spiral unit (assist tool) 20 attached to the insertion section 3 is located at the specific position or not. In other words, the position of the spiral unit 20 relative to the insertion section 3 is identified based on the sensing result of the magnetic force that acts on the magnetic sensor 72.

In one modification, a coil may be provided instead of the magnetic sensor 72 as a sensing section. In this case, a magnetic field is formed by the magnet 75 and the magnet 71, and thereby a current flows through the coil. Accordingly, a change in current flowing through the coil due to the magnet (attachment side magnet) 75 is sensed. Based on a sensing result of the current (physical quantity) that changes due to the magnet (identified element) 75, the identification section 61 determines whether or not the spiral unit (assist tool) 20 attached to the insertion section 3 is located at the specific position or not. In other words, the position of the spiral unit 20 relative to the insertion section 3 is identified based on the sensing result of the current flowing through the coil.

Figure 11:
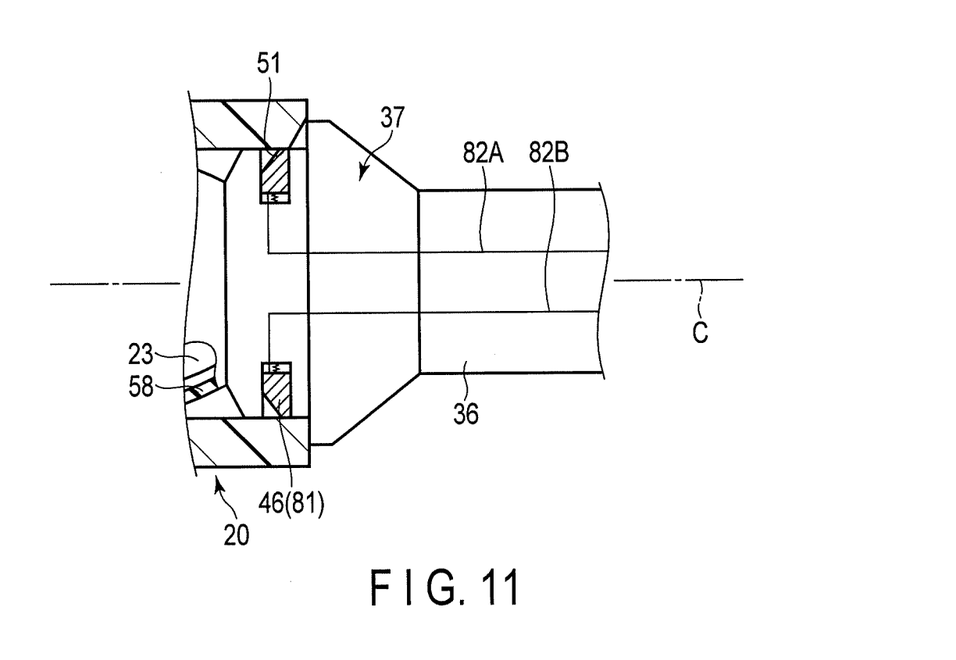
FIG. 11 is a schematic diagram showing a configuration of a proximal portion of a spiral unit according to a second modification of the second embodiment and a region of an insertion section near a moving member, in a state in which the spiral unit is attached to the insertion section at a specific position.

In a second modification of the second embodiment shown in FIG. 11, a moving member 46 is formed over a whole circumference of the insertion section 3 around the longitudinal axis C. Furthermore, a pressure sensing section 81, such as a pressure sensor, is provided on an outer peripheral surface of the moving member 46. The pressure sensing section 81 is extended over the whole circumference around the longitudinal axis C. The pressure sensing section 81 is electrically connected to an identification section 61 through electric wires 82A and 82B. Moreover, in this modification, an identified element is a pressing section 51 that exerts a pressure on the moving member 46 in a state in which the moving member 46 is located at a retracted position. In this modification, as the moving member 46 moves to the retracted position and the spiral unit 20 is attached to the insertion section 3 at a specific position (proper position), the pressing section 51 presses the pressure sensing section 81 of the moving member 46. Accordingly, a pressure of a predetermined range acts on the pressure sensing section 81. Based on the pressure that acts on the pressure sensing section 81, the identification section 61 identifies whether the spiral unit 20 is attached to the insertion section at the specific position (proper position).

Specifically, in step S102 in FIG. 9, the identification section 61 determines whether the pressure acting on the pressure sensing section 81 is in a predetermined range or not. If the pressure is in the predetermined range, it is determined that the spiral unit 20 is attached to the insertion section 3 at the specific position (proper position) in step S103.

In this modification, since the pressure sensing section 81 is provided in the insertion section 3 as a sensing section, a change in pressure acting on the pressure sensing section 81 due to the pressing section 51 is sensed. Based on a sensing result of the pressure (physical quantity) that changes due to the pressing section (identified element) 51, the identification section 61 determines whether or not the spiral unit (assist tool) 20 attached to the insertion section 3 is located at the specific position or not. In other words, the position of the spiral unit 20 relative to the insertion section 3 is identified based on the sensing result of the pressure that acts on the pressure sensing section 81.

Other Modifications

In the embodiments etc. described above, the spiral unit (20) was described as an example of the assist tool; however, the assist tool is not limited to the spiral unit (20). It is only necessary that the assist tool is detachably attached to the insertion section (3) and actuated in the state of being attached to the insertion section (3), so that a propulsion force for movement along the longitudinal axis (C) can act on the insertion section (3).

In the embodiments etc. described above, the endoscope (2) was described as an example of the insertion instrument; however, the insertion instrument is not limited to the endoscope (2). The configuration described above may be applied to, for example, an insertion device (surgical system) using a manipulator as the insertion instrument.

According to the embodiments etc. described above, the insertion device (1) includes the insertion section (3) extended along the longitudinal axis (C), and the assist tool (20) detachably attached to the insertion section (3). The assist tool (20) is actuated in a state of being attached to the insertion section (3), thereby causing a propulsion force for movement along the longitudinal axis C to act on the insertion section (3). Furthermore, the insertion section (3) is provided with the moving member (46; 46A, 46B) movable between the projecting position and the retracted position. In the state in which the assist tool (20) is attached to the insertion section (3) at the specific position, the pressing section (51; 51A, 51B) of the assist tool (20) exerts a pressure on the moving member (46; 46A, 46B), thereby holding the moving member (46; 46A, 46B) at the retracted position.

In the embodiments etc. described above, the moving member (46; 46A, 46B) is provided in the insertion section 3. However, the moving member (46; 46A, 46B) may be provided in the assist tool, such as the spiral unit 20. In this case, in the state in which the assist tool is located at the specific position relative to the insertion section 3, the moving member (46; 46A, 46B) moves from the projecting position (first position) to the retracted position (second position) by the pressure from the insertion section 3, and is held in the retracted position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
    an insertion section extended along a longitudinal axis;
    an assist tool detachably attached to the insertion section, the assist tool being configured to be actuated when attached to the insertion section, when actuated, the assist tool causing a propulsion force for movement along the longitudinal axis to act on the insertion section; and
    a moving member provided in the insertion section, the moving member being movable between a first position and a second position,
    wherein:
    the moving member is located at the first position or between the first position and the second position, in a state in which the assist tool is located at a position different from a specific position relative to the insertion section; and
    the moving member is located at the second position due to a pressure from the assist tool, in a state in which the assist tool is located at the specific position relative to the insertion section;
    the insertion section having a sensor configured to sense movement of the moving member to the second position; and
    the insertion device further comprising:
        an actuator configured to generate a driving force to actuate the assist tool; and
        a controller comprising hardware, the controller being configured to:
            determine whether the assist tool is located at the specific position based on a sensing result of the sensor; and
            control supply of electric power to the actuator only in a case in which the assist tool is determined to be located at the specific position relative to the insertion section.

2. The insertion device according to claim 1, wherein:
    the assist tool includes a pressing surface which is abuttable with the moving member; and
    the moving member moves to the second position due to abutment of the pressing surface, and thereby serves as an index indicating that the assist tool is located at the specific position relative to the insertion section.

3. The insertion device according to claim 2, wherein the pressing surface of the assist tool is provided in a proximal-side part on an inner peripheral surface of the assist tool.

4. The insertion device according to claim 1, wherein:
    the sensor includes a first electric contact, and a second electric contact which is electrically insulated from the first electric contact in a state in which the assist tool is located at the position different from the specific position relative to the insertion section; and
    the assist tool includes a conductive section which electrically connects the first electric contact and the second electric contact in a state in which the moving member is located at the second position due to an action of the pressure from the assist tool.

5. The insertion device according to claim 1, wherein:
the assist tool includes a magnet configured to generate a magnetic field in a state in which the moving member is located at the second position; and
the sensor is configured to sense at least one of the generated magnetic field and a current that flows due to generation of the magnetic field, in the state in which the moving member is located at the second position.

6. The insertion device according to claim 1, wherein:
the sensor is provided in the moving member, and is configured to sense at least a pressure; and
the assist tool is configured to cause a pressure of a predetermined range to act on the sensor in a state in which the moving member is located at the second position.

* * * * *